United States Patent [19]
Nicolais

[11] Patent Number: 6,161,695
[45] Date of Patent: *Dec. 19, 2000

[54] PROTECTIVE PACKAGING UNIT

[75] Inventor: Lawrence B. Nicolais, Niantic, Conn.

[73] Assignee: Depuy Orthopaedics, Inc., Warsaw, Ind.

[*] Notice: This patent issued on a continued prosecution application filed under 37 CFR 1.53(d), and is subject to the twenty year patent term provisions of 35 U.S.C. 154(a)(2).

[21] Appl. No.: 09/137,614

[22] Filed: Aug. 21, 1998

[51] Int. Cl.[7] .................................................. B65D 81/20
[52] U.S. Cl. .......................... 206/438; 206/524.8; 53/434
[58] Field of Search .......................... 53/403, 432, 434; 206/363, 364, 438, 439, 484, 524.8, 570, 581; 229/5.84

[56] References Cited

U.S. PATENT DOCUMENTS

| | | | |
|---|---|---|---|
| 3,358,415 | 12/1967 | Kurfirst | 53/434 |
| 4,418,514 | 12/1983 | Spann | 53/436 |
| 4,548,852 | 10/1985 | Mitchell | 53/432 |
| 4,709,819 | 12/1987 | Lattuada et al. | 53/434 |
| 4,730,726 | 3/1988 | Holzworth | 206/524.8 |
| 4,881,359 | 11/1989 | Schirmer | 53/434 |
| 5,415,340 | 5/1995 | Calvert et al. | 229/5.84 |
| 5,460,269 | 10/1995 | Bayer | 206/524.8 |
| 5,497,601 | 3/1996 | Gonzalez | 206/364 |
| 5,577,368 | 11/1996 | Hamilton et al. | 53/432 |
| 5,607,055 | 3/1997 | Bettinger | 206/524.8 |
| 5,631,036 | 5/1997 | Davis | 426/396 |
| 5,664,408 | 9/1997 | Chesterfield et al. | 53/512 |
| 5,681,317 | 10/1997 | Caldarise | 606/93 |
| 5,817,353 | 10/1998 | Guarino | 53/434 |

FOREIGN PATENT DOCUMENTS

| | | |
|---|---|---|
| 29710531 | 2/1997 | Germany. |
| 0487043 | 12/1967 | Switzerland. |
| 2121752 | 6/1982 | United Kingdom. |

*Primary Examiner*—Jim Foster
*Attorney, Agent, or Firm*—Nutter, McClennen & Fish, LLP

[57] ABSTRACT

A method is provided for protectively packaging sterilizable materials. A product to be packaged is placed within a semi-rigid, foldable packaging tray to form a package insert. The package insert is then placed within a heat-sealable container, such as a polymeric film envelope. Vacuum force is applied to evacuate the vacuum sealable container and to seal the packaging insert within the vacuum sealable container. The vacuum sealed container may then be placed within an outer, flexible packaging container and heat sealed therein. The entire package is generally sterilized after heat sealing within the outer, flexible package.

15 Claims, 4 Drawing Sheets

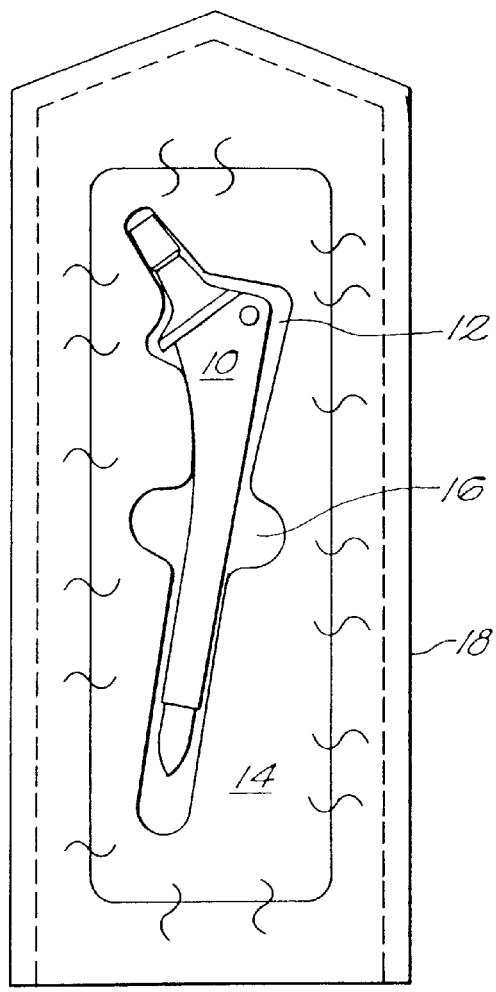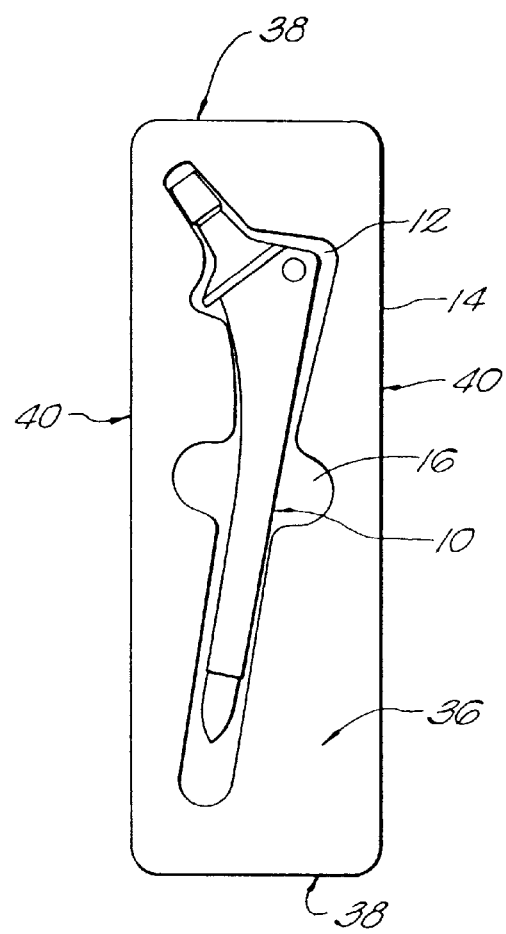
FIG. 4
FIG. 3

PROTECTIVE PACKAGING UNIT

CROSS-REFERENCE TO RELATED APPLICATIONS

Not applicable.

STATEMENT REGARDING FEDERALLY SPONSORED RESEARCH

Not applicable.

FIELD OF THE INVENTION

The invention relates to packing units, and more particularly to vacuum sealed protective packing units.

BACKGROUND OF THE INVENTION

Many packages have been designed to cushion a packaged product against shock and vibration so that the product is not damaged during the transportation and handling cycle. Such packages should provide effective protection while at the same time permit enough of a view of the product through the packaging unit for the purpose of visual product identification without opening the package.

Several types of protective packaging units are in use today. For example, some parts are simply vacuum packaged in a pouch or bag. One drawback to such packaging designs is that they tend not to provide much cushioning to the packaged product. In addition, the pouch or bag, after vacuum forming, does not have a predictable size or shape, tends to wrinkle randomly and conform closely to the packed product.

Rigid blister packs can accommodate a range of product shapes and sizes. However, they often require additional components, such as foam pads, blocks, or other inserts, to cushion the product and to occupy the space between the product and the package. The use of these pads and/or blocks tends to obstruct some or all of the view of the product and therefore is unacceptable in applications in which product visibility is essential. Blister packs also tend to yield packages that are significantly larger and bulkier than the product or products that they package.

Skin packaging is achieved by sandwiching a product between a heat-shrinkable, heat-sealable film and a porous backing. The film is heated to a plastic state as vacuum is drawn through the porous backing causing the film to seal around the perimeter of the product to the backing card. Skin packaging provides good product visibility, but it can be difficult to remove product from the packaging material that adheres to it. Opening a skin package usually requires that the package be cut and/or separated from the product, thus creating the risk that the product will be scratched or otherwise damaged during the packaging removal process. Another drawback to skin packaging is that it does not provide good product cushioning. External pads or other protective devices must be used to protect the product since protective material cannot be sealed within the skin package.

It would thus be desirable to provide a protective packaging unit that enables good product visibility while at the same time provides the product cushioning and protection.

SUMMARY OF THE INVENTION

The invention provides a method of packaging an object in such a way that the packaged object is at least partially visible within the package, and is protected against product damage during shipping and handling. Moreover, the package and its contents are sterilizable, and the packaging unit is effective to maintain the sterility of the product. An object to be packaged is first placed within a nest area formed within at least one surface of a semi-rigid packaging tray. The nest area generally has a size and shape resembling the size and shape of the object to be packaged. The packaging tray and the product to be packaged are then placed, as a unit, within a flexible, vacuum sealable container. A vacuum force is applied to the vacuum sealable container, thus drawing the container around the product and the packaging tray. The vacuum container is subsequently sealed. Optionally, the vacuum sealed container may be placed within a separate, flexible outer container, which itself is sealed by a process such as heat sealing.

An advantage of the invention is that the vacuum sealed container is tightly drawn over the product and the packaging tray, thus securely holding the product in place within the tray. Moreover, the integrity of the vacuum sealed container ensures that the product, once sterilized, will remain in a sterile environment until the package is opened.

Generally, the packaging tray is made from a deformable material such as a polymeric foam material. The vacuum sealable container is preferably made from a transparent material or a partially transparent material, and may be made from a polymer film, a foil film, or a composite polymer film/foil film.

The invention also provides a heat sealed packaging unit made according to the method of the invention.

BRIEF DESCRIPTION OF THE DRAWINGS

The foregoing features of this invention, as well as the invention itself, may be more fully understood from the following description of the drawings in which:

FIG. 3 is a top view of a package insert according to the present invention in which a product is disposed within a packaging tray;

FIG. 4 is a top view of a package insert vacuum sealed within a vacuum sealable container according to the present invention;

DETAILED DESCRIPTION OF THE INVENTION

The present invention provides a protective, flexible packaging unit that cushions packaged products from the shock and vibration typically encountered during the transportation and handling cycle. In addition to effectively protecting the packaged product from transportation and handling damage, the packaging unit of the invention enables the product to be viewed in one plane, facilitating visual inspection and identification of the product without opening the packaging material. The packaging unit of the invention is applicable to a variety of materials, particularly sterilizable components such as medical devices and prosthesis components. For purposes of illustration, however, the invention is described and illustrated with reference to a packaging unit that is specifically adapted for packaging a hip stem joint prosthesis. One of ordinary skill in the art will readily appreciate that modifications can be made to the size and shape of the packaging tray and its various components so as to accommodate the packaging of a variety of other components.

Figure 1:
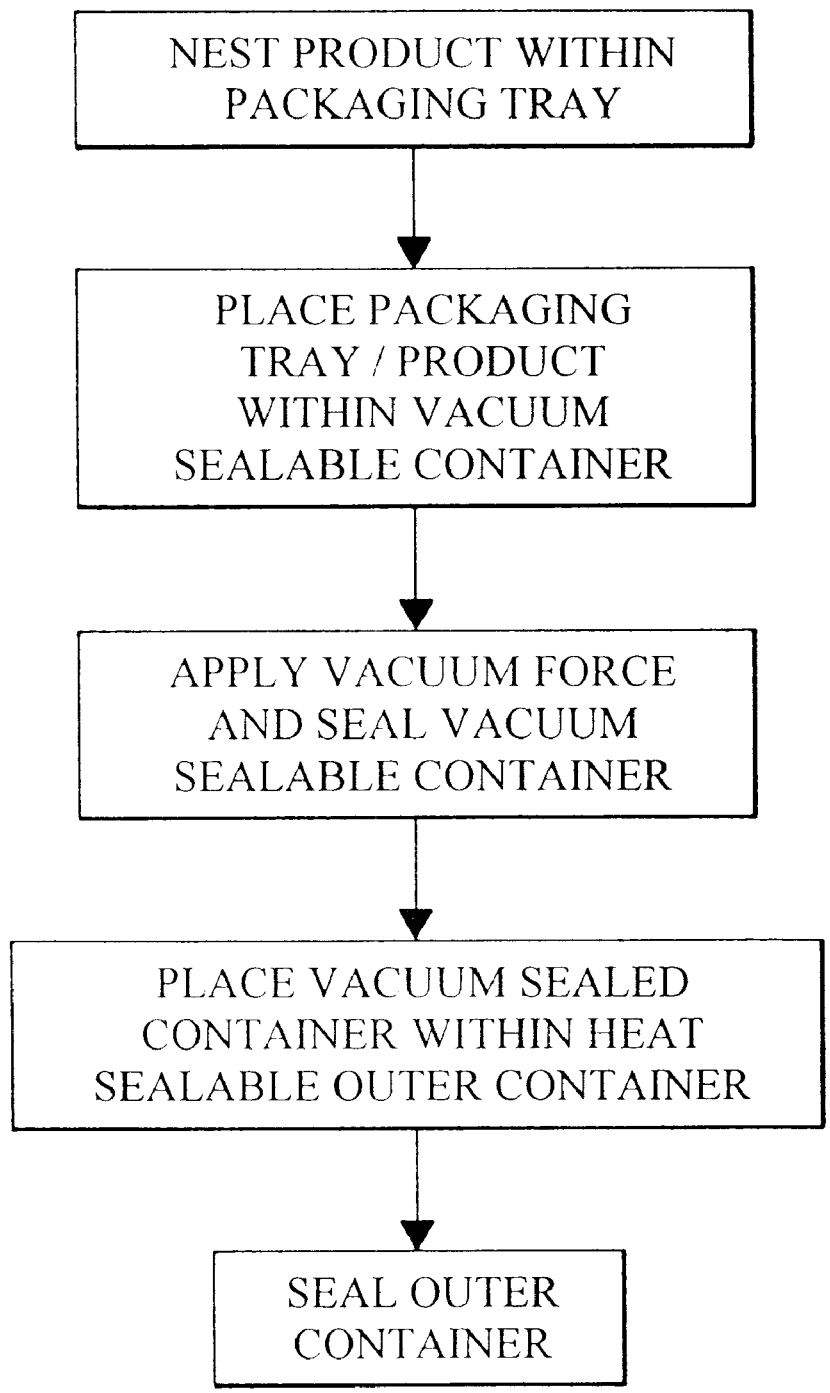
FIG. 1 is a flow chart illustrating the method of the invention.

The flow chart of FIG. 1 provides an overview of the process according to the invention. As described in FIG. 1, a product to be packaged is first placed within a nest area of a packaging tray to form a package insert. The packaging insert is then placed within a vacuum sealable container, such as a bag or envelope, having at least one opening disposed therein. A vacuum force is applied to the vacuum sealable container to evacuate the container. Then, the container is sealed hermetically. Optionally, the vacuum sealed package insert can be placed within a separate, heat sealable container which is itself sealed by a process such as heat sealing to result in a double pouch, consistent with the packaging of sterilizable medical devices.

Figure 2:
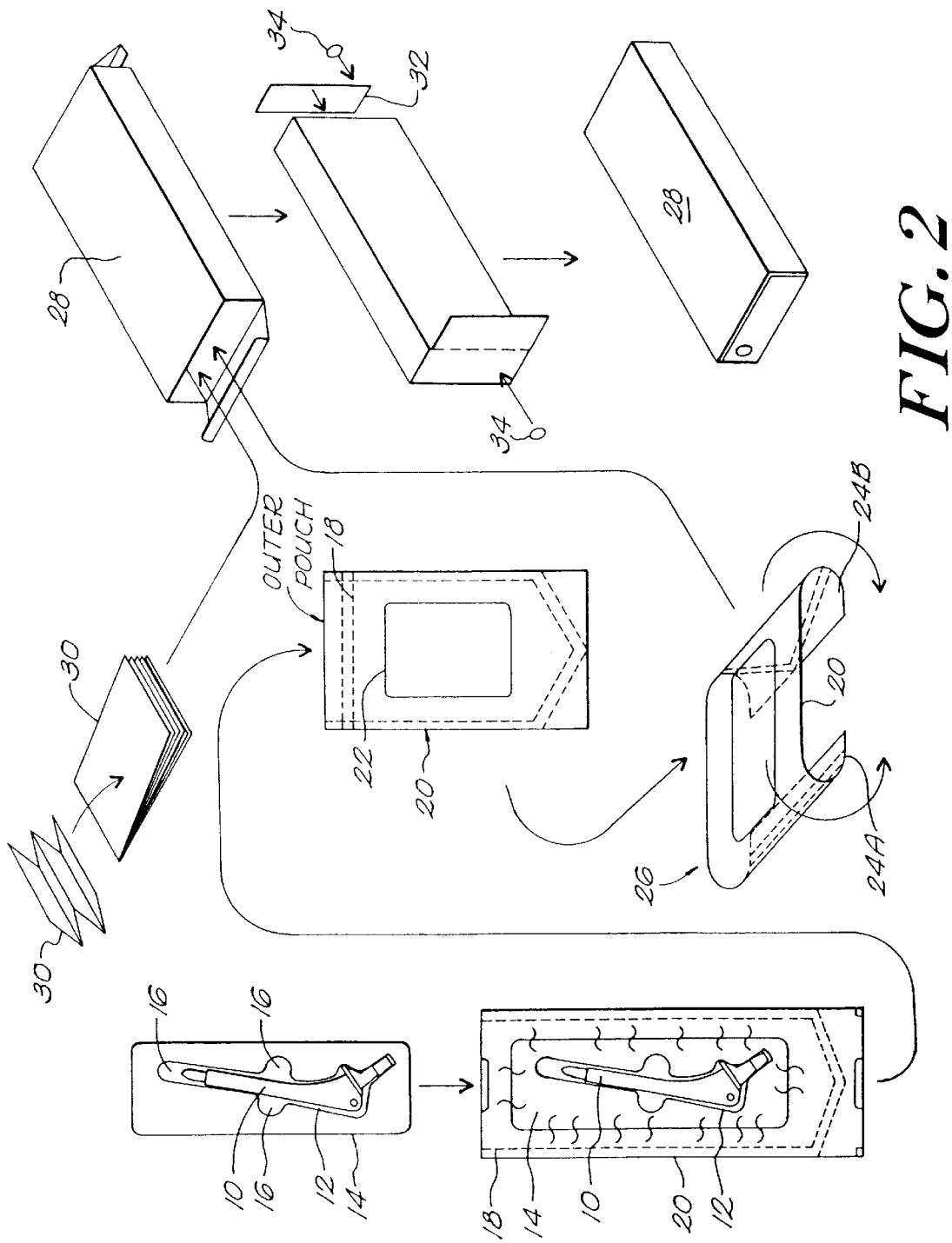
FIG. 2 is a schematic illustration of a packaging unit according to the present invention and its assembly steps.
Figure 5:
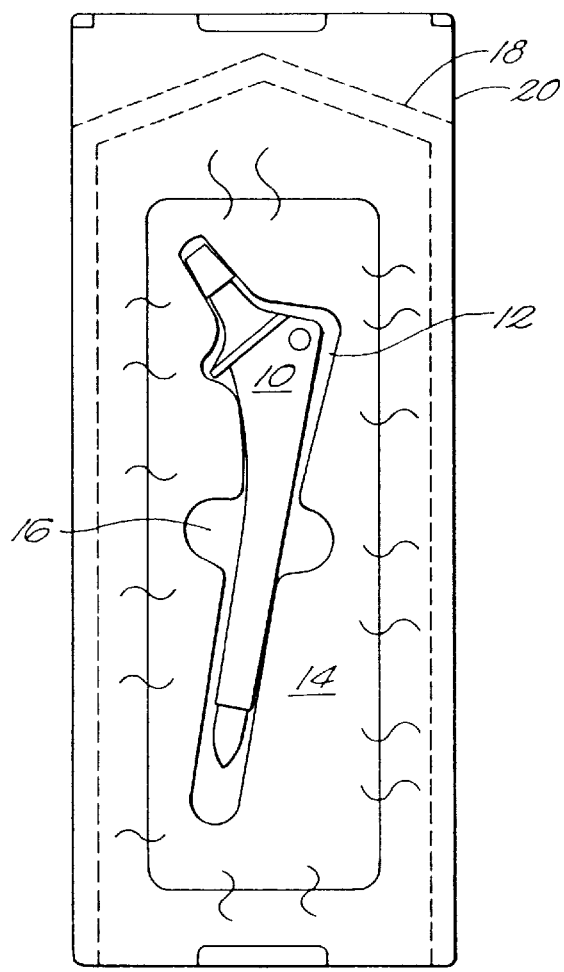
FIG. 5 is a top view of a flexible packaging unit according to the present invention.

The process of the invention, as well as the various components that form the invention, is illustrated in FIG. 2. As shown, a product 10 placed within a nest area 12 of a packaging tray 14. The nest area 12 is a depressed or recessed area in one surface of a packaging tray, and it generally conforms in size and shape to the product to be packaged. The nest area 12 may include one or more depressions 16 to enable convenient insertion and removal of the product from the packaging tray. The packaging insert 10 is then placed within a vacuum sealable container 18 (shown in FIG. 2 as being disposed within an outer container 20.) The vacuum sealable container 18 is then evacuated according to known vacuum sealing processes, and sealed. The vacuum sealed container is then placed within a flexible outer container 20 which subsequently is heat sealed. Any necessary labels 22 may then be applied to the outer surface of the outer container 20. If necessary, the ends 24A, 24B of the container may be folded over as shown in step 26 and the assembly may be placed in a shipping container 28, such as a box. In addition, product informational materials 30 may be placed within a shipping container 28 and additional product labels 32 and radiation and sterilization labels 34 may be affixed to the shipping container.

As noted above, conventional vacuum sealing procedures can be used to vacuum seal the vacuum sealable container 18. One of ordinary skill in the art can readily determine an effective range of vacuum forces that will be sufficient to hold the product securely in place during transportation and handling. Generally the vacuum force is as low as about 15 mbar, but it can be in the range of about 10 to 900 mbar. Typically, the vacuum force is exerted on the package until the package is sealed, i.e., for about 1 to 60 seconds. While the vacuum force is maintained, the package is heat sealed, preventing reinflation of the package when the vacuum is subsequently released. Techniques for heat sealing packaging material while under vacuum force are readily known and commercially available to those of ordinary skill in the art. One example of a suitable vacuum packaging apparatus is a MultiVac A342 apparatus, available from MultiVac, Inc. of Kansas City, Mo.

The packaging tray 14 used with the present invention is preferably a semi-rigid material. Packaging tray can be made from a variety of materials. Preferably, the material should have sufficient rigidity so that it possesses good structural integrity and will not deform during vacuum processing. However, it should be somewhat flexible so that it is able to absorb physical shock and mitigate vibrational forces. Suitable materials include a variety of polymer foams such as a cross linked low density polyethylene (LDPE) foam. Examples of commercially available medical grade cross linked LDPE foams include PLASTAZOTE and VOLARA. Another example of a suitable foam is ETHAFOAM.

The packaging tray 14 can assume virtually any size or shape that is necessary to meet the requirements of a given packaging solution. In the exemplary embodiment, shown in FIGS. 2–6, the packaging tray is substantially rectangular having a top surface 36, opposed short sides 38, and opposed long sides 40. The depth of the packaging tray can also vary, but generally the depth of the packaging tray 14, or at least the depth of the nest area 12, should be sufficient to enable the entirety of the packaged product 10 to be recessed below the plane of top surface 36 when the product 10 is disposed within nest area 12.

As shown in FIGS. 2 through 5, the packaging tray 14 has a nest area 12 that is formed in one surface (e.g., top surface 36) of the tray 14. The nest area 12 is large enough to accommodate the product 10, yet when the product 10 is placed into the depression formed by the nest area 12, the top surface of the product should be at or below the top surface 36 of the tray 14. This assures that the product 10 will be well cushioned within the plane formed by the packaging tray 14.

Figure 6:
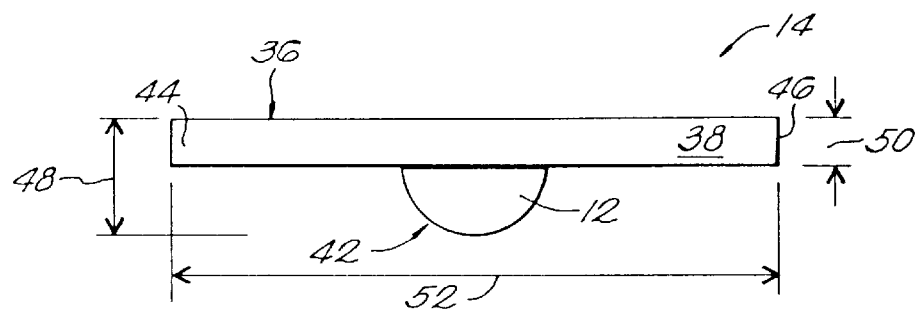
FIG. 6 is an end view of an exemplary packaging tray useful with the present invention.

As illustrated in FIG. 6, an exemplary tray 14, which for purposes of illustration may be assumed to be generally rectangular in shape, has a top surface 36 and a bottom portion 42. The bottom portion 42 is formed as a result of the nest area 12 being depressed within the tray. The packaging tray 14 further includes a flange portion 44, which defines the top portion 36 of the packaging tray. The flange portion 44 has a depth 50, which is substantially less than the overall depth 48 of the packaging tray. Usually, the flange portion depth is about one-quarter to one-half of the overall depth 48. Further, the flange portion 44 extends over the entire width 52 of the packaging tray 14, and well beyond the width of nest area 12. This construction contributes to the overall shape of the packaging tray 14 and helps protect the product from damage due to shock or vibration.

The vacuum sealable container 18 is preferably made from a flexible material that will maintain its product conforming contours throughout the expected shelf life of the package. The container 18 should be made from a flexible, low permeability material. Ideally, all or part of the vacuum sealable container 18 should be made from a transparent material. Examples of suitable materials from which container 18 may be made include flexible polymer films. Exemplary polymer materials from which the flexible film can be formed include polyester film, linear low density polyethylene film, ethylene vinyl acetate, ionomer, and nylon.

The vacuum sealable container 18 can also be made from blends and/or laminates of different materials. In one embodiment, the container 18 is formed by placing two separate sheets of polymer film on top of each other and joining them together along three sides (e.g., by heat sealing), thus forming a bag or envelope having one open end. In one embodiment, a bottom, opaque sheet is made of coextruded film of ionomer and ethylene vinyl acetate while a top, transparent sheet is made of a coextruded film of polyester and low density polyethylene.

The vacuum sealable container 18 can be made at virtually any thickness that is deemed necessary or desirable by one of ordinary skill in the art. Generally, however, the thickness of each sheet that forms a side of the vacuum sealable container 18 is in the range of about to 2 to 4 mils.

The flexible outer container 20 can likewise be made from flexible polymeric films, flexible foil films, and flexible composite polymer-foil films that are or can be made to be gas impermeable. Preferably, the outer container 20, like the vacuum sealable container 18, is made from a transparent or partially transparent polymeric film. The outer container 20 should further be capable of sealing through a heat-sealing process. Examples of suitable materials from which the outer container can be made include spun-bound polyethylene (e.g., TYVEK), polyester film, linear low density polyethylene film, ethylene vinyl acetate, ionomer, and nylon.

The flexible outer container 20 may be made of the same types of materials from which vacuum sealable container 18 is formed. In one embodiment, however, the outer container 20 is formed by placing two separate sheets of film on top of each other and joining them together along three sides (e.g., by heat sealing), thus forming a bag or envelope having one open end and dimensions large enough to accept vacuum sealed container 18. In one embodiment, a bottom non transparent sheet of film is made from TYVEK while a top, transparent sheet is made of a coextruded film of polyester and low density polyethylene.

The vacuum sealable container 18 can be made at virtually any thickness that is deemed necessary or desirable by one of ordinary skill in the art. Generally, however, the thickness of each sheet that forms a side of the outer container 20 is in the range of about 2 to 4 mils.

The present invention is advantageous because the vacuum sealing of container 18 evacuates the container and causes the material from which container 18 is made to be drawn around the packaging tray 14. Continued application of the vacuum force while sealing the container 18 enables the film from which container 18 is made to maintain the product 10 securely within the nest area 12 of the packaging tray 14.

The product 10 may be sterilized once container 18 is sealed or after vacuum sealed container 18 is placed and sealed within outer container 20. One of ordinary skill in the art will appreciate that sterilization, through gamma ray radiation or other radiation sterilization techniques, can be effected.

The present invention is applicable to a variety of products which are to be packaged. In particular, however, the invention is applicable to the packaging of medical devices such as joint prosthesis components.

Having described the preferred embodiments of the invention, it will now become apparent to one of ordinary skill in the art that other embodiments incorporating their concepts may be used. It is felt therefore that these embodiments should not be limited to disclosed embodiments but rather should be limited only by the spirit and scope of the appended claims. All publications and references cited herein are expressly incorporated herein by reference in their entirety.

What is claimed is:

1. A method of packaging a sterilizable solid medical object, comprising the steps of:

providing a semi-rigid, polymeric foam packaging tray having a flange portion defining a top surface of the packaging tray in which is formed a preexisting nest area with a predetermined shape generally resembling the shape of a solid medical object to be packaged;

placing the medical object to be packaged within the nest area of the packaging tray to form a package insert, such that the entirety of the medical object is recessed below a plane of the top surface of the packaging tray;

placing the package insert within a flexible, vacuum sealable container having at least one opening therein; and applying a vacuum force to the vacuum sealable container and simultaneously sealing the at least one opening to yield a vacuum sealed container, the vacuum force being effective to draw the vacuum sealable container into close conformity with the package insert.

2. The method of claim 1, further comprising the steps of:

placing the vacuum sealed container within an outer sealable package; and sealing the outer sealable package.

3. The method of claim 1, wherein the packaging tray is deformable.

4. The method of claim 1, wherein the vacuum sealable container is transparent.

5. The method of claim 4, wherein the vacuum sealable container is made from a polymer film selected from the group consisting of polyester, cross linked polyethylene, ethylene vinyl acetate, ionomer, nylon and blends and laminates thereof.

6. The method of claim 1, where the vacuum sealable container is a polymer film.

7. The method of claim 1, wherein the vacuum force is in the range of about 10 to 900 mbar.

8. A sterilization packaging unit, comprising:

a semi-rigid, polymeric foam packaging tray having a flange portion defining a top surface of the packaging tray in which is formed at least one preexisting nest area having a predetermined shape generally resembling the shape of a solid medical object to be packaged;

a sterilizable, solid medical object to be packaged disposed within each of the at least one nest areas such that the entirety of the medical object is recessed below a plane of the top surface of the packaging tray; and a vacuum sealed flexible container fabric enveloping the packaging tray in close conformity to the packaging tray.

9. The packaging unit of claim 8, further comprising an outer flexible package heat sealed about the vacuum sealed flexible container fabric.

10. The packaging unit of claim 8, wherein the packaging tray is deformable.

11. The packaging unit of claim 9, wherein at least one side of the vacuum sealable container is transparent.

12. The packaging unit of claim 11, wherein the vacuum sealable container is made of a polymer film selected from the group consisting of polyester, cross linked polyethylene, ethylene vinyl acetate, ionomer, nylon, and blends and laminates thereof.

13. The packaging unit of claim 8, wherein the vacuum sealable container is a polymer film.

14. The packaging unit of claim 9, wherein at least a portion of the outer flexible package is transparent.

15. The packaging unit of claim 10, wherein the polymer foam is low density polyethylene.

* * * * *